US008876685B2

(12) United States Patent
Crosby et al.

(10) Patent No.: US 8,876,685 B2
(45) Date of Patent: Nov. 4, 2014

(54) BLOOD PUMP WITH AN ULTRASOUND TRANSDUCER

(75) Inventors: Peter Andrew Crosby, New South Wales (AU); Colin Neville Sutton, New South Wales (AU); Peter Joseph Ayre, New South Wales (AU)

(73) Assignee: Thoratec Corporation, Pleasanton, CA (US)

( * ) Notice: Subject to any disclaimer, the term of this patent is extended or adjusted under 35 U.S.C. 154(b) by 89 days.

(21) Appl. No.: 12/580,091

(22) Filed: Oct. 15, 2009

(65) Prior Publication Data

US 2010/0036487 A1 Feb. 11, 2010

Related U.S. Application Data

(63) Continuation of application No. 11/924,124, filed on Oct. 25, 2007, now abandoned.

(30) Foreign Application Priority Data

Oct. 27, 2006 (AU) ................................ 2006905998

(51) Int. Cl.
| *A61N 1/362* | (2006.01) |
| *A61M 1/10* | (2006.01) |
| *A61M 1/36* | (2006.01) |
| *A61M 1/12* | (2006.01) |

(52) U.S. Cl.
CPC ............. *A61M 1/101* (2013.01); *A61M 1/3663* (2013.01); *A61M 2205/3523* (2013.01); *A61M 1/122* (2013.01)
USPC .......................................................... 600/16

(58) Field of Classification Search
CPC ...... A61M 1/00; A61M 1/101; A61M 1/1072; A61M 1/1074; A61M 1/1082
USPC ............................ 600/16–18; 604/4.01–6.16; 417/1–410.5, 279–311, 43; 73/861.18–861.31; 623/3.1, 3.13, 3.14, 623/3.15, 3.18, 3.24, 3.25
See application file for complete search history.

(56) References Cited

U.S. PATENT DOCUMENTS

| 4,914,959 | A | * | 4/1990 | Mylvaganam et al. ..... 73/861.28 |
| 5,046,503 | A | * | 9/1991 | Schneiderman .............. 600/505 |
| 5,211,546 | A | | 5/1993 | Isaacson et al. |
| 5,230,341 | A | * | 7/1993 | Polaschegg ................... 600/481 |
| 5,289,821 | A | | 3/1994 | Schwartz |
| 5,370,509 | A | | 12/1994 | Golding et al. |
| 5,423,741 | A | * | 6/1995 | Frank ............................... 604/26 |
| 5,423,747 | A | | 6/1995 | Amano |
| 5,644,093 | A | * | 7/1997 | Wright et al. ................ 73/866.5 |
| 5,695,471 | A | | 12/1997 | Wampler |

(Continued)

FOREIGN PATENT DOCUMENTS

| CA | 2237203 | 3/1998 |
| EP | 1 354 606 | 10/2003 |

(Continued)

*Primary Examiner* — Christopher D Koharski
*Assistant Examiner* — Roland Dinga
(74) *Attorney, Agent, or Firm* — Squire Patton Boggs (US) LLP

(57) ABSTRACT

A blood pump including an ultrasonic sensor mounted in or on a blood contacting surface of the blood pump. The ultrasonic sensor measures blood velocity and reports information to a blood pump controller. The ultrasonic sensor is directed to measure blood velocity in an inflow cannula connected to the blood pump.

22 Claims, 2 Drawing Sheets

(56) References Cited

U.S. PATENT DOCUMENTS

| | | | |
|---|---|---|---|
| 5,840,070 | A | 11/1998 | Wampler |
| 5,865,749 | A * | 2/1999 | Doten et al. ............... 600/443 |
| 6,027,498 | A | 2/2000 | Mutch et al. |
| 6,066,086 | A | 5/2000 | Antaki et al. |
| 6,071,093 | A | 6/2000 | Hart |
| 6,080,133 | A | 6/2000 | Wampler |
| 6,100,618 | A | 8/2000 | Schoeb et al. |
| 6,120,537 | A | 9/2000 | Wampler |
| 6,142,752 | A * | 11/2000 | Akamatsu et al. ............ 623/3.1 |
| 6,158,984 | A | 12/2000 | Cao et al. |
| 6,190,319 | B1 * | 2/2001 | Goldowsky ............... 600/437 |
| 6,217,541 | B1 | 4/2001 | Yu |
| 6,227,797 | B1 * | 5/2001 | Watterson et al. ........... 415/107 |
| 6,234,772 | B1 | 5/2001 | Wampler et al. |
| 6,234,998 | B1 | 5/2001 | Wampler |
| 6,264,635 | B1 | 7/2001 | Wampler et al. |
| 6,277,078 | B1 | 8/2001 | Porat et al. |
| 6,293,901 | B1 * | 9/2001 | Prem ............................. 600/17 |
| 6,368,083 | B1 | 4/2002 | Wampler |
| 6,443,884 | B1 * | 9/2002 | Miyawaki ..................... 600/17 |
| 6,443,983 | B1 * | 9/2002 | Nagyszalanczy et al. ... 623/3.28 |
| 6,623,420 | B2 | 9/2003 | Reich et al. |
| 6,688,861 | B2 | 2/2004 | Wampler |
| 6,918,870 | B1 | 7/2005 | Hunyor et al. |
| 6,949,066 | B2 * | 9/2005 | Bearnson et al. ............... 600/16 |
| 6,991,595 | B2 | 1/2006 | Burke et al. |
| 7,138,776 | B1 | 11/2006 | Gauthier et al. |
| 7,645,225 | B2 | 1/2010 | Medvedev et al. |
| 2001/0009645 | A1 | 7/2001 | Noda |
| 2002/0183628 | A1 | 12/2002 | Reich et al. |
| 2003/0223879 | A1* | 12/2003 | Yanai et al. ..................... 417/43 |
| 2004/0084398 | A1 | 5/2004 | Breitschwerdt et al. |
| 2004/0084399 | A1 | 5/2004 | Cook et al. |
| 2004/0234397 | A1 | 11/2004 | Wampler |
| 2004/0254469 | A1 * | 12/2004 | Shkarlet et al. ............... 600/459 |
| 2007/0231135 | A1 | 10/2007 | Wampler et al. |
| 2008/0080983 | A1 | 4/2008 | Wampler et al. |
| 2008/0085184 | A1 | 4/2008 | Wampler et al. |
| 2008/0089779 | A1 | 4/2008 | Wampler et al. |
| 2008/0089797 | A1 | 4/2008 | Wampler et al. |

FOREIGN PATENT DOCUMENTS

| | | |
|---|---|---|
| JP | 2002-224066 | 8/2002 |
| JP | 2004-278375 | 10/2004 |
| WO | WO 97/29795 | 8/1997 |
| WO | WO 00/69490 | 11/2000 |
| WO | WO 01/05023 | 1/2001 |
| WO | WO 01/12070 | 2/2001 |
| WO | WO 03/015609 | 2/2003 |
| WO | WO 2004/028593 | 4/2004 |

* cited by examiner

BLOOD PUMP WITH AN ULTRASOUND TRANSDUCER

TECHNICAL FIELD

The present invention relates to an implantable blood pump with an ultrasonic transducer to detect and measure blood flow, and to enable ultrasound imaging.

BACKGROUND OF THE INVENTION

In the past, blood pumps have been used successfully to treat patients with late stage congestive heart disease or failure. Commonly, pulsatile blood pumps or continuous flow rotary blood pumps have been connected in parallel to a patient's heart to supplement or assist their heart in pumping blood through the patient's circulatory system. These types of blood pump are been commonly called left ventricular assist devices (LVADs) because they are generally connected between the left ventricle of the patient's heart and the aorta to offload the heart.

A preferred example of an implantable rotary blood pump is described in U.S. Pat. No. 6,227,797 (Watterson et al). This pump is a continuous flow blood pump which includes a hydrodynamically suspended impeller that rotates to impart a centrifugal force on the blood in the pumping chamber. The blood is propelled to the rest of the circulatory system. The impeller described within this specification is generally shaft-less and this feature may significantly reduce the areas or regions stagnation for the blood travelling through the pump. U.S. Pat. No. 6,227,797 describes a blood pump suitable for implantation within the body of the patient.

The concept of an implantable ultrasonic sensor for detecting blood flow is detailed within U.S. Pat. No. 5,865,749 (Doten et al). This disclosure describes an implanted ultrasonic sensor that directly measures the blood flow within a patient's circulatory system by the attachment of the sensor onto a blood vessel.

U.S. Pat. No. 5,423,747 (Amano) describes an ultrasonic sensor and an extracorporeal blood pump being used simultaneously to inform a doctor or clinician of any problems or events experienced by a patient. These events may include significant reductions in blood flow from over-pumping the ventricle by the pump or clotting of the blood. When an event is detected, the doctor or clinician may immediately take action to remedy the problem by slowing the pumping speed set-point or stopping the blood pump. This arrangement has several significant disadvantages. The first disadvantage is that the arrangement requires the blood pump and ultrasonic sensor to be extracorporeal relative to the patient, which generally means the patient is bed ridden and restricted to a hospital environment. The second disadvantage is that the described ultrasonic sensor and blood pump are separate components and are not part of an integrated system. In addition, the arrangement described has a relatively large surface area of blood contacting regions which may increase the risk of thrombogenesis or clotting. The third problem is that the described system does not include an automatic control system using the measurements from the ultrasonic transducer to allow a pump controller to automatically adjust the pumping speed set-point of the blood pump without the doctor or clinician manually adjusting the speed, therefore the described system relies entirely on the doctor or clinician detecting a problem and taking immediate action to remedy said problem.

The present invention aims to or at least address or ameliorate one or more of the disadvantages associated with the above mentioned prior art.

SUMMARY OF THE INVENTION

According to a first aspect the present invention is a blood pump including a ultrasonic sensor mounted in or on a blood contacting surface of said blood pump, said ultrasonic sensor measures blood velocity and reports information to a blood pump controller and wherein said ultrasonic sensor is directed to measure blood velocity in an inflow cannula connected to the blood pump.

Preferably the ultrasonic sensor is mounted on a lower surface of the blood pump.

Preferably the blood pump is a rotary blood pump and includes a shaft-less rotary impeller.

Preferably said blood pump controller adjusts a pumping speed setpoint of the blood pump in accordance with the detected blood flow in the inflow cannula.

Preferably said blood pump is fully implanted within the body of the patient.

Preferably said blood pump controller is implanted within the patient and wirelessly transmits power and data with an external system.

Preferably the blood pump controller derives haematocrit values from the detected blood flow, actual speed of blood pump, and power consumed by blood pump.

Preferably the blood pump controller calculates the imminence of a collapse of the left ventricle or occlusion based the detected values of blood flow.

Preferably the blood pump controller pulses the pumping speed setpoint of the blood pump synchronously with the pulsing of blood flow detected in the inflow cannula.

According to a second aspect the present invention is a blood pump including at least one ultrasonic sensor mounted within a portion of the blood pump, wherein the sensor is aimed at the cavity of a ventricle and is capable of detecting or measuring motion of the either the aortic or mitral valves.

Preferably said ultrasonic sensor is connected to a pump controller, which maintains the pumping speed of said pump, and wherein pump controller adjusts pumping state in accordance the detected motion of the aortic or mitral valves.

According to a third aspect the present invention is a pump including at least one ultrasonic sensor mounted within a portion of the blood pump, wherein the sensor measures blood flow and a pump controller, which is connected to the sensor and pump, calculates haematocrit based on measured flow.

BRIEF DESCRIPTION OF THE DRAWINGS

Embodiments of the present invention will now be described with reference to the accompanying drawings wherein.

BRIEF DESCRIPTION OF THE PREFERRED EMBODIMENTS

Figure 1:
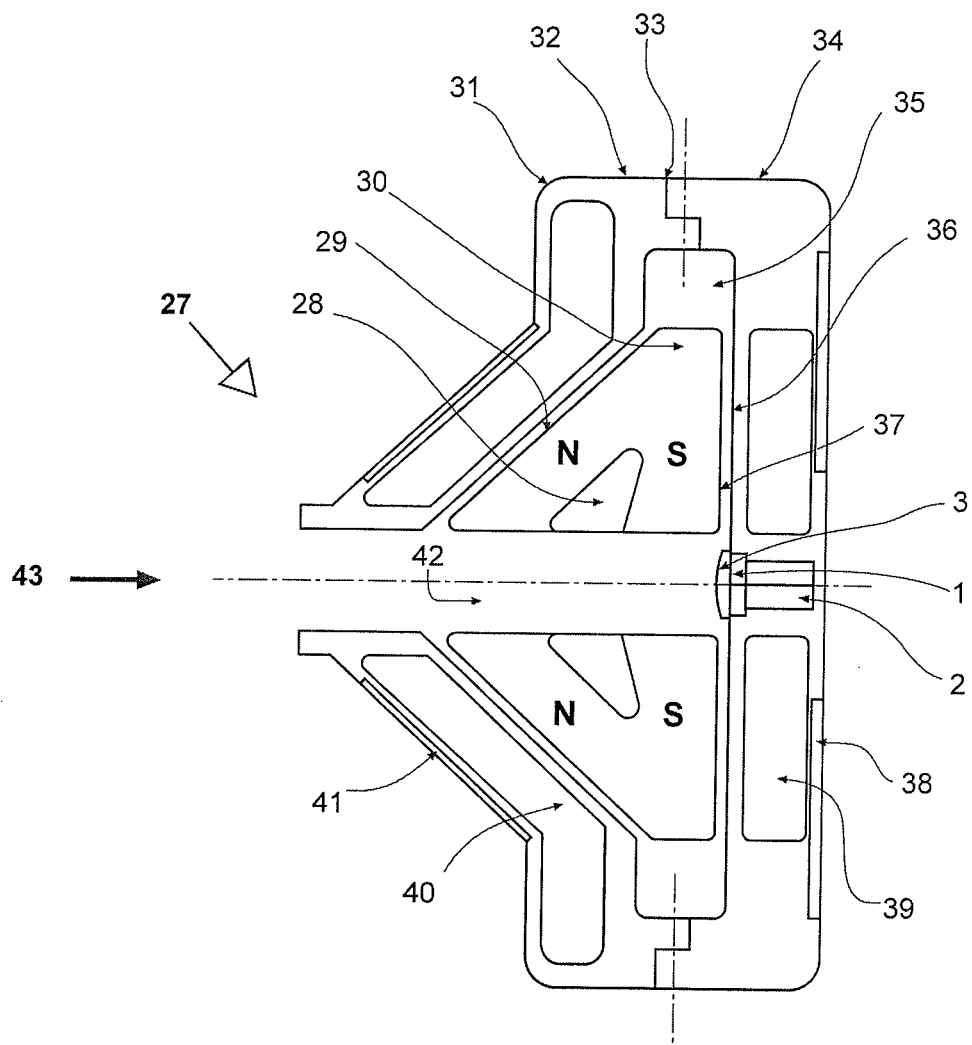
FIG. 1 depicts a cross sectional view of a first embodiment of the present invention.
Figure 2:
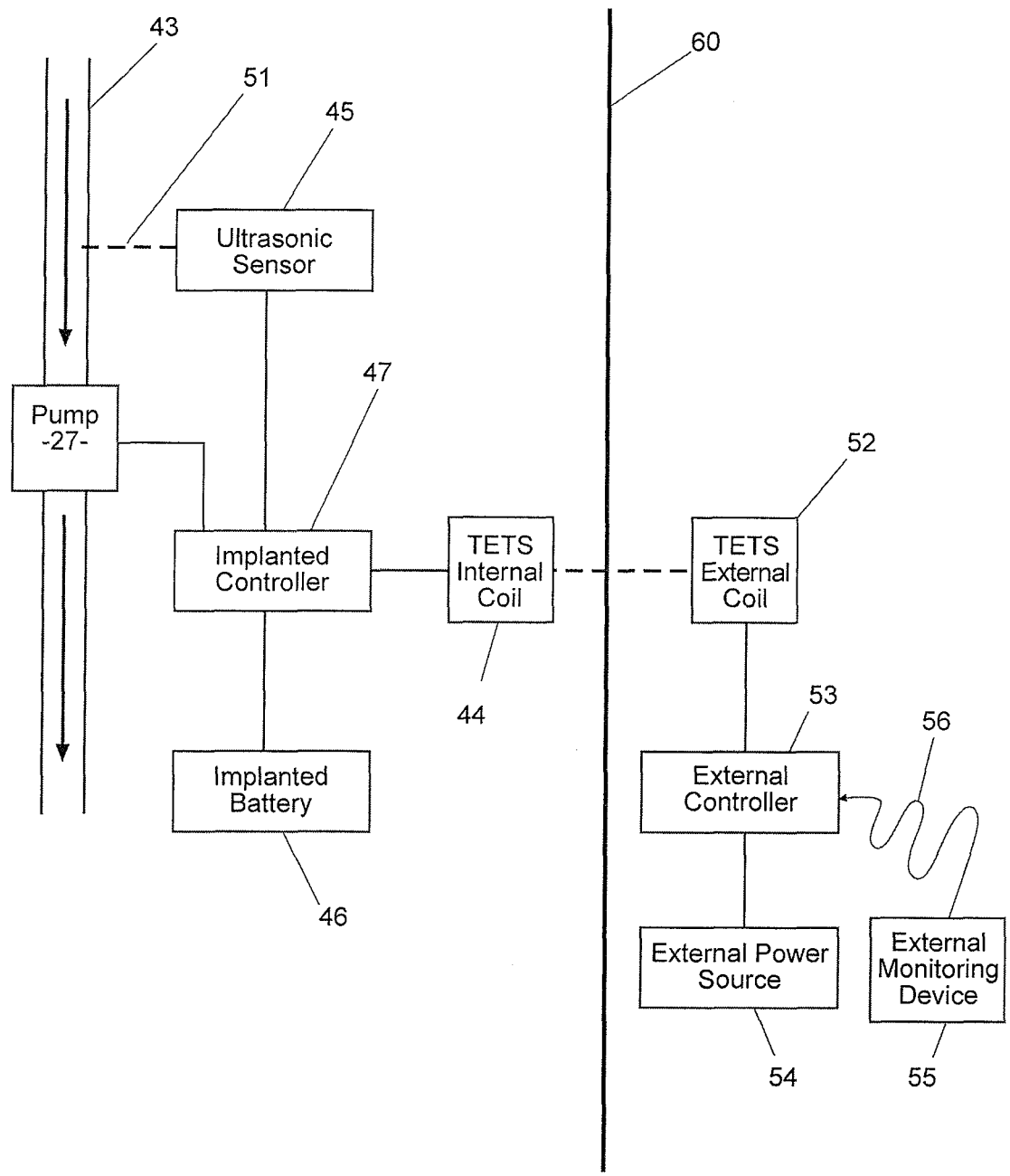
FIG. 2 depicts a schematic view of the first embodiment when implanted within a patient.

A first preferred embodiment of the present invention is depicted in FIGS. 1 & 2. In this first preferred embodiment, a blood pump 27 includes an impeller 30 mounted within a cavity 37 within a housing 32.

The most preferred blood pump for use with this first preferred embodiment is similar to the blood pump described within U.S. Pat. No. 6,227,797 (Watterson et al). When in use, impeller 30 is magnetically urged to rotate by upper and lower stator coil assemblies 40 & 39 acting on permanent rare earth magnets 28 embedded within each blade of the impeller 30.

When in operation, impeller 30 is hydrodynamically suspended by thrust forces generated by tapered edges of the blades forming a "restriction area" as the blades rotate. The "restriction area" forms in a region of relatively high pressure in gaps 29 & 36 and this pressure forces impeller 30 away from housing 32 at an angle normal relative to the angle of the inner housing surface.

Furthermore, the preferred impeller 30 is shaft-less, see central region 42, minimizing regions of stagnation that are commonly associated with regions of low flow such as shafts or mechanical pivot bearings. Preferably, impeller 30 includes four generally "shark fin" shaped blades which are generally positioned in a circular arrangement by interconnecting struts.

Blood pump 27 operates by magnetically rotating impeller 30 about an axis of rotation in housing 32. The motion of the rotating blades imparts a centrifugal force on blood entering pump 27 via inflow cannula 43. The centrifugal force displaces the blood outwardly from the centre of pump 27 to the outer wall of housing 32. The outer wall generally includes an outlet, which is in turn connected to an outflow cannula 35.

Preferably, blood pump 27 is fully or wholly implanted within the body of a patient. Inflow cannula 43 is connected to the left ventricle of the heart through a hole cored by a surgeon into the apex of the left ventricle (not shown). Outflow cannula 35 is generally connected to the patient's aorta by suturing (not shown). The net result is that blood pump 27 acts in parallel to the normal pumping function of the heart and assists the left ventricle.

Upper and lower stator coil assemblies 40, 39 are mounted on opposed sides of impeller 30 in the housing 32. The stator coil assemblies 39 & 40 generally comprise phase coils constructed of electrically conductive wire capable of inducing electromagnetism when a current is applied. Preferably, there are three phase coils mounted on the upper and lower portions of housing. The electromagnetic efficiency of the coil assemblies may be increased by the further mounting of yokes 41 & 38 on the outside of the stator coil assemblies.

Preferably, housing 32 includes upper and lower portions 31, 34 joined hermetically by seal 33. The seal 33 is preferably achieved by laser welding of the housing portions which are preferably made of Titanium alloy.

An ultrasonic transducer 1 may be mounted in the centre of the base plate located on the inner wall of the lower portion 34 of housing 32. Mounting the ultrasonic transducer 1 within blood pump 27 significantly reduces the area of blood contacting surface used by this arrangement, when compared to having a prior art arrangement where the blood pump and ultrasonic transducer are separately implanted components or items. Preferably, the ultrasonic transducer 1 is mounted behind a relatively thin titanium wall in the hermetically sealed space within housing 32. As will be apparent to a person skilled in the art, an ultrasound coupling lens 2 is used to couple the ultrasound energy from the transducer 1 to the titanium base-plate, and if necessary an ultrasound lens 3 is used to focus and direct the ultrasound beam such that the ultrasound beam is directed up along the axis of rotation of impeller 30 and insonates the incoming blood in the inflow cannula. In this embodiment, this is achieved because the impeller 30 is shaft-less and the ultrasonic transducer 1 has an uninterrupted view (or path) into the inflow cannula 35 from the aforementioned base plate.

In an alternative embodiment, the ultrasound transducer and coupling means may be mounted inside the blood pump and contacting the blood directly. This is possible in the earlier described blood pump 30 because impeller 30 is shaft-less, and therefore the ultrasound transducer if mounted inside the blood filled chamber of pump 27, does not occlude the flow or inhibit free movement of impeller 30.

The ultrasound coupling lenses, dimensions, frequency, and power of the ultrasound system is determined by the distances needed to be insonated. Such determination is easily done by someone skilled in the art and is dependent on the overall dimensions of blood pump 27.

Since the ultrasound signal is at a different frequency to the signal used to energize the motor, it may be able to capacitively and/or inductively couple the ultrasound signals to the phase wires within the stator assemblies 39 & 40, thus obviating the need for additional wires to pump 27. Alternatively, the ultrasound electronics may be included in the hermetically sealed housing 32 of pump 27, obtain energy from the phase wires used to energize the motor, and wirelessly communicate with the outside world via the use of radio frequency communications or other standard wireless interfaces (eg. Bluetooth™ technology).

In an alternative embodiment, blood pump 27 may include a phased array ultrasound transducer system which would allow direct imaging through housing 32 of blood flowing into pump 27 and the system components, even up to the left ventricular cavity.

Preferably, an ultrasound pulse may be transmitted by the ultrasonic transducer at predetermined time intervals along the axis of rotation of the shaft-less impeller 30. The reflected ultrasonic echoes may be used to determine:

a) the velocity of the blood at different points along the axis of the impeller by the use of standard ultrasound Doppler technology, including all the way up the inlet cannula 43 and into the left ventricle;

b) real-time movement and function of the left ventricle wall; and, depending on location of pump 27 and inlet cannula 43, the leaflets of the mitral and/or aortic valves (this is commonly referred to as M-mode ultrasound);

c) using spectral analysis of the returned ultrasonic echoes, the solid matter content of the blood, which is related directly to hematocrit; and/or d) if an array system is used, an image of the blood path all the way up to the left ventricle and valves.

These data may be used as input parameters to a control system, and in particular may be used to:

a) directly measure flow velocity and, by knowing the cross sectional area of the inflow cannula, therefore calculate volume blood flow eg: in liters per minute;

b) from flow, speed and power, derive hematocrit from the pump head pressure vs flow relationships (commonly referred to as H-Q curves);

c) use the spectral characteristics of the ultrasonic echoes to also determine hematocrit, and thereby provide a cross check (mutual recalibration);

d) directly determine presence or incipience of ventricular suction by measuring flow and/or determining movements of the left ventricular free wall;

e) detect occlusion of the inflow cannula 43;

f) determine a difference between measured flow and derived flow (from the H-Q curves) and thereby determine when the pump may be occluded; and/or g) used to control pulsatility of flow by synchronizing pump speed changes with movement of the LV wall and/or changes in blood velocity.

Further, FIG. 2 depicts the first preferred embodiment implanted within a patient. Blood pump 27, as per FIG. 1, is connected to the circulatory system of the patient by an inflow cannula 43 and outflow cannula 35. Pump 27 is controlled by implanted controller 47, which sets an optimal pumping speed set-point for pump 27 and regulates its speed at the set-point. The implanted controller 47 is preferably connected to ultrasonic transducer 1 which is within the housing of the pump, but for schematic simplicity is shown as a separate component. Preferably, implanted controller 47 receives data from ultrasonic transducer 1 and uses these data to detect an actual measured blood flow in the inflow cannula 43. From these data, implanted controller 47 may be able to derive suction events, hematocrit levels, occlusion, or the general motion of the left ventricle.

Preferably, implanted controller 47, pump 27 and transducer 1 are powered by a rechargeable implanted battery 46. All of the implanted components of this system are implanted below the skin layer 60 of a patient. The implanted components of the system are powered by and communicate data with the external environment using a transcutaneous energy transmission system (commonly referred to as 'TETS'). TETS includes an implanted coil 44 of wire and an external coil 52 of wire mounted in a parallel orientation on either side of the skin layer in close proximity. When a current is induced in one coil, the other coil also experiences an inducement to create a current. Using the TETS, it is possible to transmit power and data across the skin layer of the patient without the need for a permanent wound created by percutaneous lead arrangements. Using the TETS, the system also includes an external system comprising an external controller 53 and external power source 54. The external power source 54 may be another battery pack or a connection to mains power. The external controller 53 may function as a backup system for the implanted controller 47 and may also be capable of retrieving and interrogating data from the implanted controller 47 and transmitting to other systems such as other computers, and the internet.

When a patient presents for follow up, it is desirable for the attending physician or other health care professional to monitor current and historical performance of the LVAD system. This may be performed using a monitoring device eg. laptop computer 55, which communicates with external controller 53 via a link 56 (by physical cable or wireless technology). In one embodiment, the communication between the controller 53 and the laptop computer 55 could be over a long distance such as via the internet.

During the monitoring process, the external monitoring means 55 obtains data from the implantable controller and ultrasound system via the external controller (or directly). These data might include historical records of blood velocity and flow, haematocrit, alarm conditions and the like. The data may also include real time information about blood velocity and flow, and if the ultrasound system includes the capacity to create an image, then that image would be displayed on the external monitoring means.

Additionally, ultrasonic transducer 1 may be preferably aimed at the cavity within the right or left ventricles of the patient's heart. If the ultrasonic transducer 1 is angled and orientated properly, the transducer 1 may be able to visualise the blood flow within the ventricle. More specifically, it may be possible to adjust the orientation of the sensor to visualise, detect or measure the opening and closing of either the aortic or mitral valves (in the case of the left ventricle). The detection of this motion of the valves may be then feedback into the control system which is managing the pumping speed of the bloodpump. Preferably, the control system may adjust the pumping speed of the blood pump so to allow the valves of the heart to function normally by opening and closing thus reducing the incidence of thrombogenesis occurring around the valves.

The above description, detail only some of the embodiments of the present invention. Modifications may be obvious to those skilled in the art and may be made without departing from the scope and spirit of the present invention.

The invention claimed is:

1. A blood pump comprising:
    a housing containing an impeller, the housing including an inflow conduit and walls that form a hermetically sealed space of the housing; and
    an ultrasound sensor disposed within the hermetically sealed space and coupled to a thin wall forming a portion of the hermetically sealed space;
    wherein the sensor is located directly beneath the inflow conduit and oriented so that the sensor insonates blood flow in an inflow cannula when the pump is in use.

2. The blood pump of claim 1, wherein the pump is a centrifugal-type pump.

3. The blood pump of claim 1, wherein the impeller is a shaftless impeller.

4. The blood pump of claim 1, wherein the sensor is capacitively or inductively coupled to phase wires of a motor of the pump so as to enable transmission of sensor signals along the phase wires.

5. A blood pump comprising:
    a housing containing an impeller, an inflow conduit and walls forming a hermetically sealed space of the housing; and
    an ultrasound sensor disposed within the hermetically sealed space and coupled to a thin wall forming a portion of the hermetically sealed space,
    wherein the sensor is surrounded by a restriction area adapted to form an area of high pressure for hydrodynamically suspending the impeller from the housing when the pump is in use; and
    wherein the impeller is located between the sensor and the inflow conduit.

6. The blood pump of claim 5, wherein the pump is a centriftigal-type pump.

7. A blood pump comprising:
    a housing;
    a shaftless impeller disposed within the housing and configured to rotate about an axis of rotation; and
    an ultrasound sensor disposed within the housing and arranged to direct an ultrasound beam up along the axis of rotation when the pump is in use.

8. The blood pump of claim 7, wherein the sensor is located beneath an inflow conduit.

9. The blood pump of claim 8, wherein the impeller is between the inflow conduit and the sensor.

10. The blood pump of claim 7, wherein the sensor is capacitively or inductively coupled to phase wires of a motor of the pump so as to enable transmission of sensor signals along the phase wires.

11. The blood pump of claim 7, wherein the pump includes a passageway extending along the axis of rotation and leading to an inflow cannula, wherein the ultrasound sensor is oriented to point through the passageway.

12. The blood pump of claim 7, the sensor further including a lens configured for focusing an acoustic signal along the axis of rotation.

13. The blood pump of claim 7, wherein the sensor is contained within a hermetically sealed housing.

14. The blood pump of claim 7, wherein the sensor is disposed within the housing in such a manner as to come into contact with a fluid when the pump is in use.

15. A blood pump comprising:
a housing containing an impeller and an inflow conduit, the impeller having an axis of rotation; and
an ultrasound sensor mounted within the housing so that the axis of rotation passes through the ultrasound sensor, wherein the ultrasound sensor is oriented to provide an unobstructed view of an inflow cannula for transmitting acoustic pulses into, and receiving reflected ultrasonic echoes from the inflow cannula for determining the pumping state of the pump.

16. The blood pump of claim 15, wherein the sensor is in contact with a fluid when the pump is in use.

17. The blood pump of claim 15, wherein the impeller is a shaftless impeller forming an axial passageway leading to the inflow cannula, wherein the ultrasound sensor is oriented to point along the axial passageway.

18. The blood pump of claim 15, wherein the sensor is surrounded by a restriction area adapted to form an area high pressure for hydro-dynamically suspending the impeller from the housing when the pump is in use.

19. The blood pump of claim 18, wherein the pump is a centrifugal-type pump.

20. The blood pump of claim 15, the sensor further including a lens configured for focusing an acoustic signal along an axial passageway.

21. The blood pump of claim 15, further including a controller for receiving a first signal from a motor of the pump and second signal from the ultrasound sensor,
wherein the controller is configured for deriving a first estimate of hematocrit based on motor speed derived from the first signal, motor power and a relationship between head pressure and flow characteristics for the pump, and a second estimate of hematocrit based on a spectral analysis of the second signal, and providing a cross-check of hematocrit by comparing the first estimate of hematocrit to the second estimate of hematocrit.

22. A blood pump comprising:
a housing containing an impeller;
an ultrasound sensor mounted within the housing and along an axis of rotation of the impeller; and
a controller for receiving a first signal from a motor of the pump and second signal from the ultrasound sensor,
wherein the controller is configured for deriving a first estimate of hematocrit based on motor speed derived from the first signal, motor power and a relationship between head pressure and flow characteristics for the pump, and a second estimate of hematocrit based on a spectral analysis of the second signal, and providing a cross-check of hematocrit by comparing the first estimate of hematocrit to the second estimate of hematocrit.

* * * * *